United States Patent
Zunker et al.

(10) Patent No.: US 6,679,831 B1
(45) Date of Patent: Jan. 20, 2004

(54) RESILIENT INCONTINENCE INSERT AND A METHOD OF MAKING THE SAME

(75) Inventors: MaryAnn Zunker, Oshkosh, WI (US); Herb F. Velazquez, Neenah, WI (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 28 days.

(21) Appl. No.: 09/675,460

(22) Filed: Sep. 28, 2000

(51) Int. Cl.[7] ............ A61F 2/00; A61M 31/00
(52) U.S. Cl. ................................... 600/29; 604/517
(58) Field of Search ............ 604/904, 385.17, 604/385.18, 514–517; 600/29–31; 606/191, 197

(56) References Cited

U.S. PATENT DOCUMENTS

| | | | |
|---|---|---|---|
| 2,938,519 A | 5/1960 | Marco |  |
| 3,646,929 A | 3/1972 | Bonnar |  |
| 4,019,498 A | 4/1977 | Hawtrey et al. |  |
| 4,139,006 A | 2/1979 | Corey |  |
| 4,266,546 A | * 5/1981 | Roland et al. | ............... 604/365 |
| 4,920,986 A | 5/1990 | Biswas |  |
| 5,007,894 A | 4/1991 | Enhorning |  |
| 5,036,867 A | 8/1991 | Biswas |  |
| 5,045,079 A | 9/1991 | West |  |
| 5,386,836 A | 2/1995 | Biswas |  |
| 5,609,559 A | 3/1997 | Weitzner |  |
| 5,609,586 A | 3/1997 | Zadini et al. |  |
| 5,618,256 A | 4/1997 | Reimer |  |
| 5,659,934 A | 8/1997 | Jessup et al. |  |
| 5,755,906 A | 5/1998 | Achter et al. |  |
| 5,785,640 A | 7/1998 | Kresch et al. |  |
| 5,795,346 A | 8/1998 | Achter et al. |  |
| 5,807,372 A | * 9/1998 | Balzar | ............... 604/385.18 |
| 5,816,248 A | 10/1998 | Anderson et al. |  |
| 6,039,716 A | 3/2000 | Jessup et al. |  |
| 6,039,828 A | 3/2000 | Achter et al. |  |
| 6,090,038 A | 7/2000 | Zunker et al. |  |
| 6,090,098 A | 7/2000 | Zunker et al. |  |
| 6,095,998 A | 8/2000 | Osborn, III et al. |  |
| 6,142,928 A | 11/2000 | Zunker et al. |  |

FOREIGN PATENT DOCUMENTS

| | | |
|---|---|---|
| EP | 0 460 807 A2 | 12/1991 |
| EP | 0 264 258 B1 | 4/1992 |
| EP | 0 498 912 A1 | 8/1992 |
| EP | 0 363 421 B2 | 10/1995 |
| EP | 0 714 271 B1 | 5/1998 |
| WO | WO 88/10106 | 12/1988 |
| WO | WO 98/06365 | 2/1998 |
| WO | WO 00/36996 | 6/2000 |
| WO | WO 00/37012 | 6/2000 |
| WO | WO 00/37013 | 6/2000 |

* cited by examiner

*Primary Examiner*—Weilun Lo
*Assistant Examiner*—C L Anderson
(74) *Attorney, Agent, or Firm*—Brinks Hofer Gilson & Lione; G. Peter Nichols

(57) ABSTRACT

An expandable vaginal insert device for reducing the occurrence of female urinary incontinence. The vaginal insert device includes at least a resilient member capable of expanding to transmit pressure to the urethro-vaginal myofascial area. Optionally, the device may include one or more non-absorbent layers in addition to the resilient member. The resilient member and any additional layers are formed into an elongated member, which may be then be shaped into a M-shaped shaped profile or a dome-shaped profile.

20 Claims, 8 Drawing Sheets

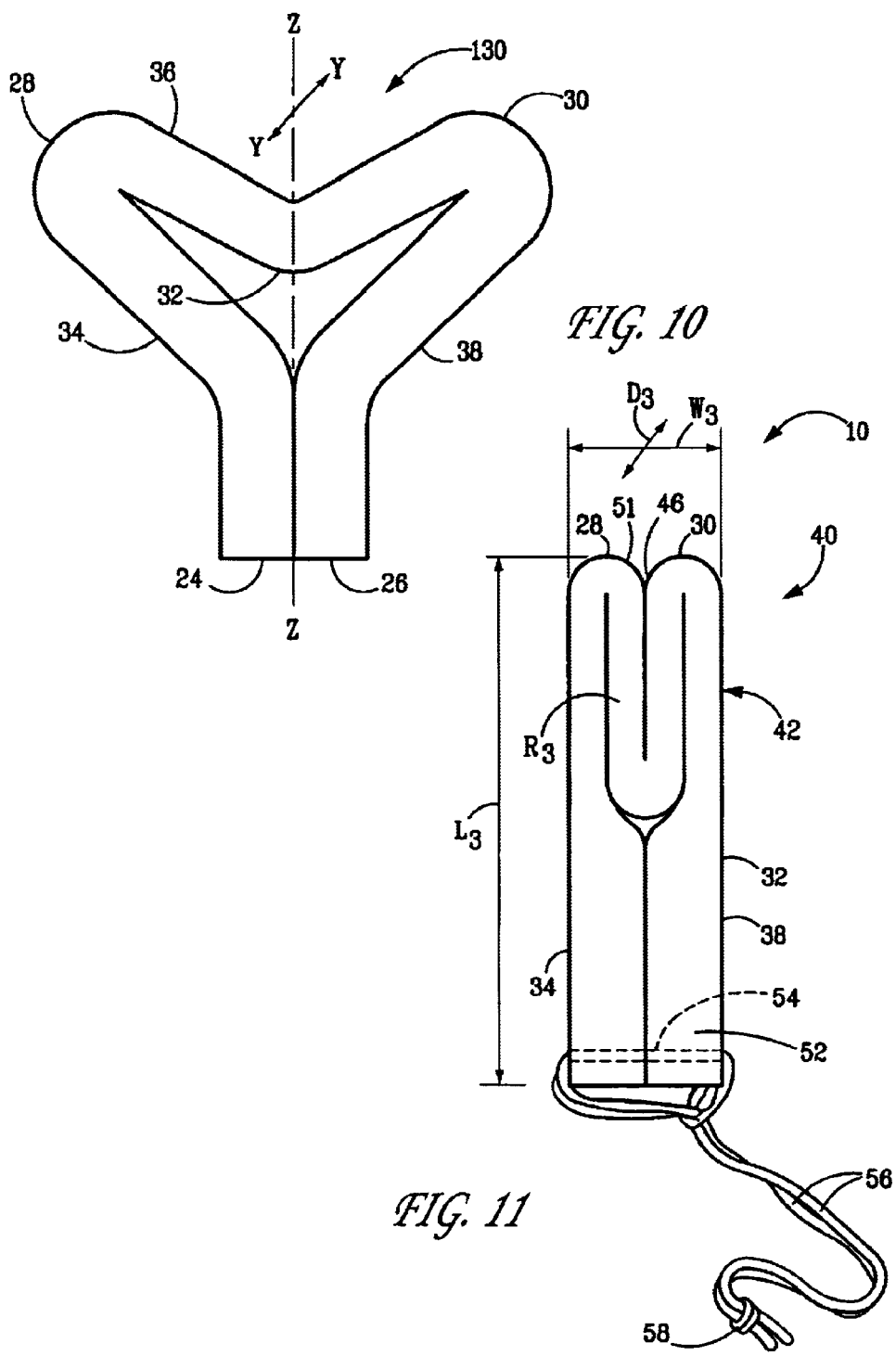

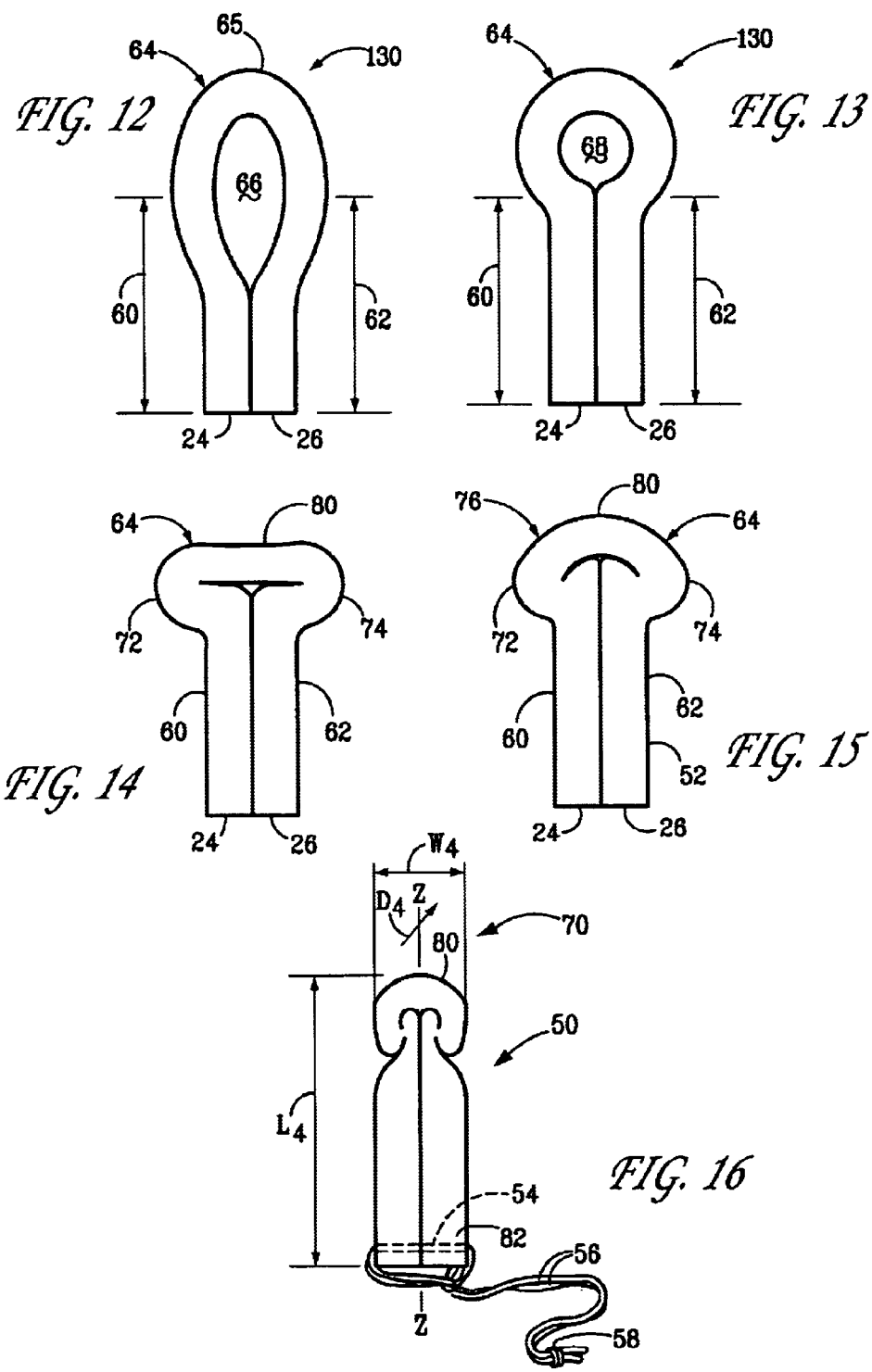

RESILIENT INCONTINENCE INSERT AND A METHOD OF MAKING THE SAME

FIELD OF THE INVENTION

This invention relates to an expandable urinary incontinence device and a method of making the device. More specifically, this invention relates to a non-absorbent urinary incontinence device which is designed to be placed in a woman's vagina for providing support to a woman's urethra to prevent the involuntary urine loss commonly associated with stress urinary incontinence.

BACKGROUND

Some women, especially women who have given birth to one or more children, and older women, can experience incidences of involuntary urine loss due to stress urinary incontinence or combined stress and urge incontinence. A sneeze or cough can increase the intra-abdominal pressure impinging on a person's bladder and cause the involuntary release of urine. The frequency and severity of such urine loss can increase as the muscles and tissues near the urethro-vaginal myofascial area grow weaker. It has also been recognized that the urinary sphincter muscle, which is located at the upper end of the urethra adjacent to the bladder, works well at sealing off the passing of urine from the bladder to the urethra when it has a round or circular cross-sectional configuration. However, when this passageway becomes distorted into a cross-sectional configuration having more of an elliptical or oval appearance, the sphincter muscle can not close properly, therefore, the tendency for involuntary urine loss increases.

As the world's female population ages, there is an ever increasing need for a non-surgical procedure to reduce the involuntary urine loss commonly associated with "stress urinary incontinence." Today, there are a number of products available for this purpose. Essentially all of these products can only be purchased with a prescription and they need to be physically inserted and/or adjusted by a medical doctor or a nurse practitioner in order to perform correctly.

In view of the general lack of commercially available, non-prescription urinary incontinence devices, it is recognized that there is a need for a urinary incontinence device which can be purchased without a prescription. There is also a need for a urinary incontinence device which is uncomplicated and therefor more user friendly and can be managed by the consumer without the intervention of a medical practitioner. Furthermore, there is a need for a urinary incontinence device which is easy for women to insert into and remove from their bodies, more comfortable to wear and provide psychological and realistic assurance that it is capable of properly performing over an extended period of time.

SUMMARY

According to one aspect of the invention, a urinary incontinence device includes a resilient member and a non-absorbent. The non-absorbent and the resilient member are formed into a layered elongated member having a non-absorbent layer and a resilient member layer, wherein a first surface of the resilient member is adjacent and substantially coextensive with a surface of the non-absorbent. The layered elongated member has a first end, a second end, a first portion located adjacent to the first end, a second portion located adjacent to the second end, and a third portion located between the first and second portions. The elongated member is folded upon itself such that the first and second ends are aligned substantially adjacent to one another.

In another aspect of the invention, a urinary incontinence device includes a non-absorbent resilient member formed into an elongated member. The elongated member has a first end, a second end, a first portion located adjacent to said first end, a second portion located adjacent to said second end, and a third portion located between said first and second portions. The elongated member is folded upon itself such that said first and second ends are aligned substantially adjacent to one another.

In yet another aspect of the invention, a method of making a urinary incontinence device is provided. The method includes cutting a resilient member into a desired configuration and then aligning the resilient member upon a non-absorbent such that the resilient member and the non-absorbent are substantially coextensive to form an elongated member having first and second ends. The elongated member is folded upon itself such that said first and second ends are aligned adjacent to one another. The folded elongated member is then compressed into an elongated pledget having an insertion end and a trailing end with the resilient member located at least in the insertion end, whereby the resilient member is capable of expanding at least a portion of the pledget to provide a supportive backdrop for a women's urethra when the pledget is inserted into a vagina.

Other aspects of the invention will become apparent in view of the appended claims.

BRIEF DESCRIPTION OF THE DRAWINGS

FIG. 10 is a side view of an elongated member after it has been folded into an M-shaped profile.

FIG. 11 is a side view of the elongated member shown in FIG. 10 after it has been compressed into a pledget and has a withdrawal member attached to the first and second ends.

FIG. 12 is a side view of an elongated member after it has been folded in half along its length and a closed loop is formed.

FIG. 13 is a side view of the folded elongated member shown in FIG. 12 after the first and second portions are brought into contact with one another and a smaller closed loop is formed.

FIG. 14 is a side view of the elongated member shown in FIG. 13 after the closed loop is transformed into a dome shape.

FIG. 15 is side view of the elongated member shown in FIG. 14 after the edges of the dome shaped third portion are folded downward around the first and second portions.

FIG. 16 is a side view of the elongated member shown in FIG. 15 after it has been compressed into a pledget and has a withdrawal member attached to the first and second ends.

DETAILED DESCRIPTION

Urinary incontinence devices, such as those depicted in FIGS. 11 and 16, respectively, are designed to be inserted into a woman's vagina and expand so as to relieve or eliminate the involuntary passage of urine through the urethra from the bladder. The expansion of the non-absorbent urinary incontinence device provides a stable backdrop to the musculature and body tissue located near the urethro-vaginal myofascial area and causes the urethra to be compressed upon itself during episodes of increased intra-abdominal pressure. In addition, the expansion of the urinary incontinence device in the vagina will assist the urinary sphincter muscle in maintaining a circular cross-sectional configuration. When this circular cross-sectional configuration is maintained, the sphincter muscle can close properly and decrease the tendency for the involuntary escape of urine due to stress urinary incontinence.

Figure 1:
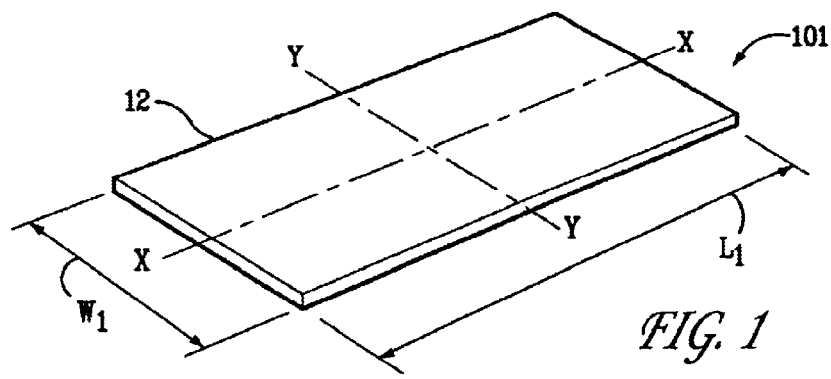
FIG. 1 is a perspective view of a resilient member used to form a urinary incontinence device.
Figure 2:
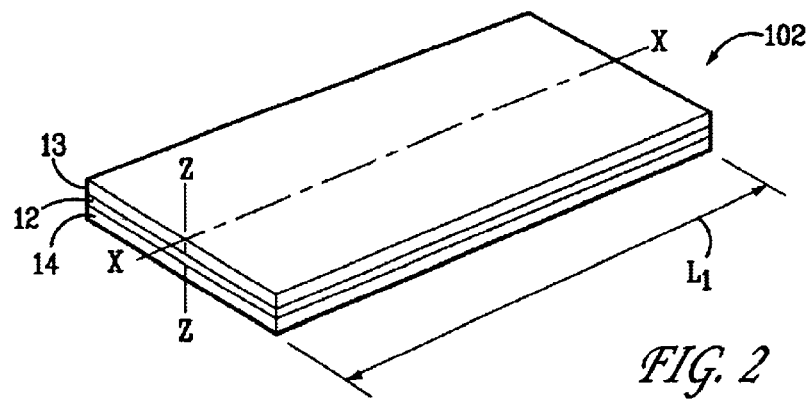
FIG. 2 is a perspective view of a resilient member sandwiched between two non-absorbents to form a laminate-like structure.
Figure 3:
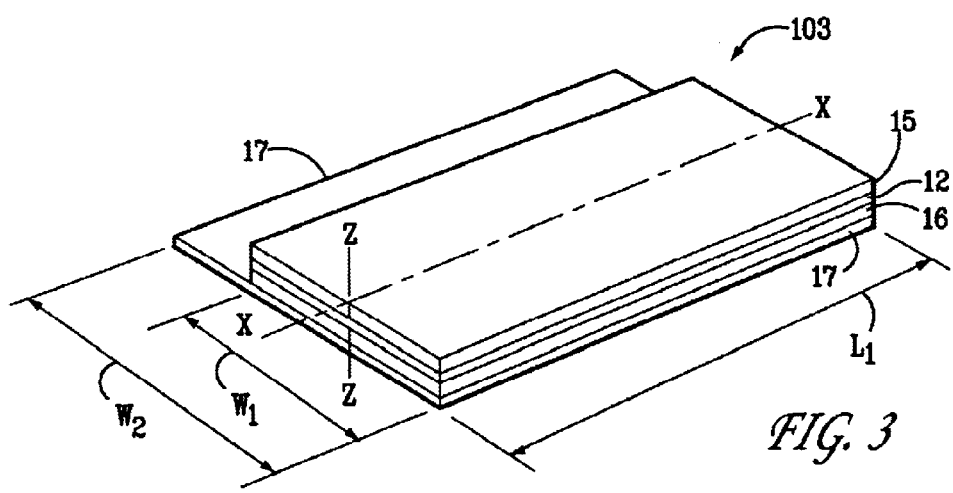
FIG. 3 is a perspective view of the structure of FIG. 2 after a cover material has been added.

Referring to FIGS. 1–3, the expandable urinary incontinence devices of the present invention at least include a resilient member 12. In other embodiments as described below, the urinary incontinence device may also include nonabsorbents 13, 14, 15, and/or 16, and a cover 17.

FIG. 1 illustrates the starting structure 101 of a urinary incontinence device made solely from a resilient member 12. The resilient member 12 can be non-absorbent or at least partially absorbent of body fluids. However, there is no functional advantage to making the resilient member 12 absorbent because the urinary incontinence device does not function in a similar manner as does a catamenial tampon. In fact, the urinary incontinence device functions entirely different from an absorbent catamenial tampon.

The resilient member 12 can be a natural or synthetic material which has the ability to quickly recover or return to approximately its original shape and/or dimension. Such change in the resilient member 12 can be created by changes in the intra-abdominal pressure as a result of laughing, sneezing, coughing, or the like. A resilient material is a material which can return to or resume its original shape or position after being bent, stretched or compressed. The resilient member 12 should also exhibit elasticity and flexibility so that it can be stretched or compressed and still retain the capability of returning to approximately it's original shape.

Two natural materials from which the resilient member 12 can be formed include natural rubber and wool. The number of synthetic materials from which the resilient member 12 can be formed is much greater. Synthetic materials which can be used include polyolefins, polyurethanes, polyethylene oxide (PEO), polyvinyl alcohol (PVA) as well as blends thereof. The resilient member 12 can also be formed from resilient fibers constructed from polyolefin based fibers, polyethylene oxide fibers, hydrophobic rayon fibers and the like, which preferably will have characteristics similar to those of a resilient foam. The resilient fibers can be formed from twisted, curled or cross-linked cellulose fibers or a mixture thereof. Furthermore, the resilient member 12 may be formed from either an open cell or a closed cell foam.

The resilient member 12 can also be made from a wettable foam. An open cell foam which works well and has good resilient properties is commercially available under the trademark ACQUELLO®. "ACQUELL" is sold by Sentinel Products Corporation having an office located at 70 Airport Road, Hyannis, Mass. 02601. A polyethylene closed cell foam having good flexibility characteristics also works well. This foam is commercially sold under the trademark VOLARA®. "VOLARA" is available from Voltex, a Division of Sekisui America Corporation having an office located at 100 Shepard Street, Lawrence, Mass. 01843.

The resilient member 12 should also be capable of having what is known as "dry and wet" expansion characteristics. In other words, the resilient member 12 should be made from a material which is capable of expanding or contracting back to or towards its original configuration in a dry state, a wet state or in a semi-dry-wet state. Dry expansion of the urinary incontinence device is beneficial in that the device does not have to be wetted by body fluid before the resilient member 12 is capable of expanding within the vagina.

In FIG. 1, the resilient member 12 is depicted as rectangular in cross-section. However, the resilient member 12 can have a square, circular, oval or any other desired cross-sectional configuration. Preferably, the resilient member 12 will have a uniform thickness and width. If desired, the dimensions of the resilient member 12 do not have to be uniform.

The resilient member 12 has a length $L_1$ and a width $W_1$. The length $L_1$ is preferably about 5 inches (127 mm) to about 10 inches (254 mm), more preferably about 6 inches (152.4 mm) to about 9 inches (228.6 mm), and most preferably about 6.75 inches (171.5 mm) to about 8.25 inches (209.5 mm). The width $W_1$ depends in part upon whether the resilient member 12 first being folded (e.g., see FIG. 4) folded and/or rolled (see e.g, FIG. 8) before being shaped into a urinary incontinence device. If the resilient member 12 is to be shaped into a urinary incontinence device without first being folded and/or rolled, it preferably will have a width $W_1$ of about 0.5 inches (12.7 mm) to about 1.5 inches (38.1 mm), and most preferably, about 1.0 inches (25.4 mm). If the resilient member 12 is to be folded once as in FIG. 4, it will generally have a width $W_1$ of about 1.0 (25.4 mm) to about 3.0 inches (76.2 mm), and most preferably about 2.0 inches (50.8 mm). More folds will require a wider resilient member.

FIG. 2 illustrates an alternate starting structure of a urinary incontinence device made from a three layer laminate 102. The laminate 102 includes a resilient member 12 sandwiched between a first nonabsorbent 13 and a second nonabsorbent 14. The first nonabsorbent 13 is adjacent to a first surface of the resilient member, and the second nonabsorbent 14 is adjacent to a second surface of the resilient member opposite the first surface. The second non-absorbent layer 14 is an optional element, especially where the laminate as a whole will be folded over upon itself along a longitudinal axis.

The layers of the laminate 102 are sized and arranged to be substantially coextensive with each other. As used herein, the phrase "substantially coextensive" means that the individual layers have either the same or about the same length and width dimensions. However, some minor dimensional variations may be present. For instance, the width of the layers may vary slightly so that when folded (as in FIG. 5), the edges of the layers will be substantially flush. Or as shown in FIG. 3, the width of the layer 17 is extended to allow for it to be later folded over upon itself.

The non-absorbents 13, 14 are constructed from materials that exhibit little, and preferably, no absorbent characteristics. The non-absorbents 13, 14 differ from a catamenial tampon in that they do not function to absorb body fluid. Instead, the non-absorbents 13, 14 are designed to cover the resilient member 12, and the combined structure is designed to bridge across the vagina and support the musculature and body tissue located in the urethro-vaginal myofascial area. By doing so, the urethra can be compressed upon itself sufficiently to interrupt the flow of urine and support can be provided to the urinary sphincter muscle so that it can function properly.

The non-absorbent 13 and the non-absorbent 14 may each be the same material, or they may be different materials. The non-absorbents 13, 14 may be in the form of a fibrous carrier or a cover material.

For purposes of this invention, a non-absorbent fibrous carrier is defined as a material wherein the fibers do not absorb significant quantities of moisture within the fiber itself. It is to be recognized that virtually all materials will absorb some small quantity of moisture. A fiber is considered to be nonabsorbent for present purposes if it will intrinsically gain no more than about 6 percent in weight when a bone dry fiber is maintained at 21° C. and at 65 percent relative humidity for 24 hours. Non-absorbent fibrous carrier materials include but are not limited to nylons, rayons, spun cellulose, LYCRA®, KEVLAR®, carbon fibers and the like. "LYCRA" and "KELVAR" are trademarks of E. I. DuPont de Nemours & Company which has an office at 1007 Market Street, Wilmington, Del. 19801. One such fibrous carrier is a web made from bicomponent fibers which are commercially available from Chisso Corporation having an office at 1411 Broadway, 35th floor, New York, N.Y. Such fibers are sold under the name "Chisso ESC Bicomponent Fiber" and consist of a polypropylene core surrounded by a polyethylene sheath. Fibers that work well have a denier of 3 and are 38 millimeters in length. Other bicomponent fibers made from polypropylene, polyethylene, etc. are commercially available from suppliers such as Exxon and Dow Chemical, as well as from other vendors.

The non-absorbents 13, 14 could also be an absorbent fibrous carrier material such as a cotton/rayon blend which has been chemically treated with a surfactant to make it non-absorbent. However, materials comprised of truly non-absorbent fibers work best.

Alternately, the non-absorbents 13, 14 may be in the form of a liquid-permeable or liquid-impermeable cover material. When the cover is liquid-impermeable, it serves to block body fluids from contacting the non-absorbents 13, 14. Since the resilient member 12 is not designed to absorb any body fluid, it is not necessary that the cover be liquid-impermeable. Liquid permeable materials include woven and nonwoven materials having a porous substrate. Woven materials include textile fabrics which can be made from rayon, cotton, or polyolefins. The polyolefins can be either staple or continuous filaments. The nonwoven materials can include spunbond, bonded carded webs and hydroentangled webs. Spunbond and bonded carded webs are commercially sold by Kimberly-Clark Corporation having an office at 401 N. Lake Street, Neenah, Wis. 54956. Another nonwoven material which can be used as the cover is formed from 100 percent polyester fibers held together by a binder. This material is known as a through-air bonded carded web (TABCW) including about 40% polyester fibers with a denier of 6, and about 60% bicomponent fibers with a denier of 3. A particularly preferred TABCW is manufactured by Kimberly Clark Corporation of Neenah, Wis.

The cover can also be constructed from a liquid-impermeable material. A good liquid-impermeable material is a micro-embossed, polymeric film, such as polyethylene or polypropylene. Bicomponent films can also be used. A preferred liquid-impermeable material is polyethylene film. The thickness of the cover can range from between about 0.1 mm (0.004 inch) to about 5 mm (0.20 inch), preferably less than about 0.5 mm (0.02 inch), and most preferably, less than about 0.2 mm (0.008 inch).

FIG. 3 illustrates another alternate starting structure for a urinary incontinence device. A four-layer laminate 103 includes a resilient member 12 sandwiched between two fibrous carriers 15, 16, and an outer cover 17. The top fibrous carrier 15 is an optional layer, especially where the laminate as a whole is folded or rolled upon itself along a longitudinal axis. The outer cover 17 provides a smooth outer surface which may or may not be chemically treated to facilitate insertion and/or removal into and out of a woman's vagina. Although the cover 17 is substantially coextensive with the other layers of the laminate 103, the cover 17 should have a width $W_2$ which is greater than the width $W_1$ of the other layers. The purpose of the greater dimension for the width $W_2$ is that it allows the cover 17 to be folded over upon itself and be bonded to itself by heat, pressure, a combination of heat and pressure, or by some other conventional means known to those skilled in the art. If the cover 17 is formed from a material which does not readily bond to itself, an adhesive, glue or other bonding or fastening medium can be used. If desired, the outer cover 17 may be simply folded over upon itself. Suitable materials for the outer cover 17 are the same liquid-permeable or liquid-impermeable cover material discussed above.

The resilient member structure 101 of FIG. 1, or the laminates 102, 103 of FIGS. 2 and 3, respectively may be formed into an elongated member before shaping into a urinary incontinence device. This can be done by simply initially cutting the layers into an suitable dimension for forming the elongated member without having to perform any further preparation such as folding or rolling. Alternately, the elongated member may be formed by folding and/or rolling the layers.

Figure 4:
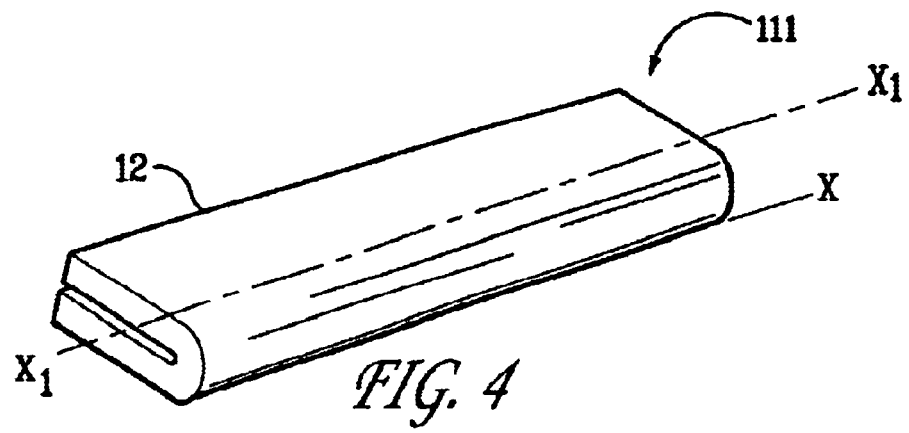
FIG. 4 is a perspective view of the structure of FIG. 1 after being folded along its longitudinal central axis.
Figure 5:
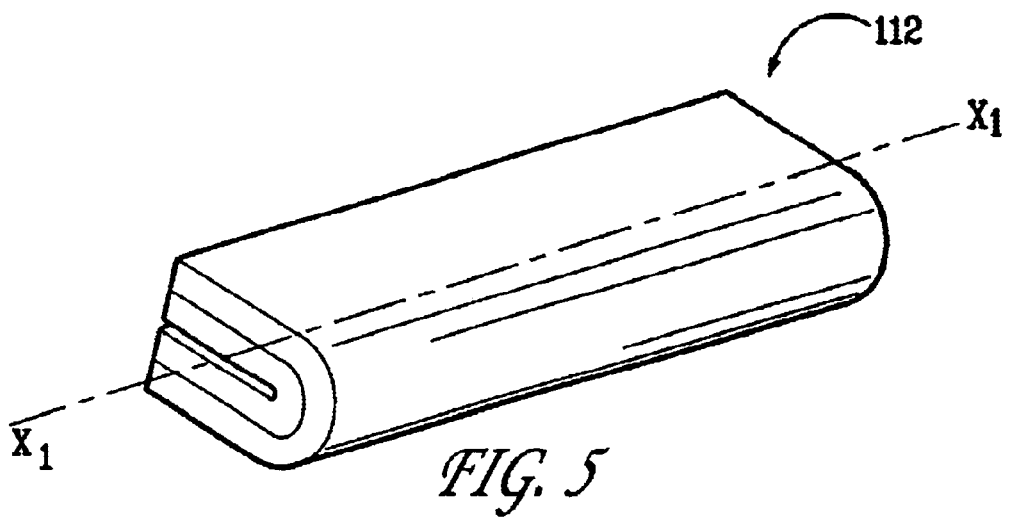
FIG. 5 is a perspective view of the combination shown in FIG. 2 after being folded along its longitudinal central axis.

FIG. 4 illustrates the resilient member 12 of FIG. 1 folded along its central longitudinal axis X-X to form an elongated member 111. FIG. 5 illustrates the laminate of FIG. 2 folded along its central longitudinal axis X-X to form an elongated member 112. The folding in either case creates an elongated member that may be shaped into a urinary incontinence device. Alternately, either of the elongated member 111, 112 may be folded again (not shown) along its new central longitudinal axis $X_1$-$X_1$, forming a twice folded elongated member that can then be shaped into a urinary incontinence device.

Figure 6:
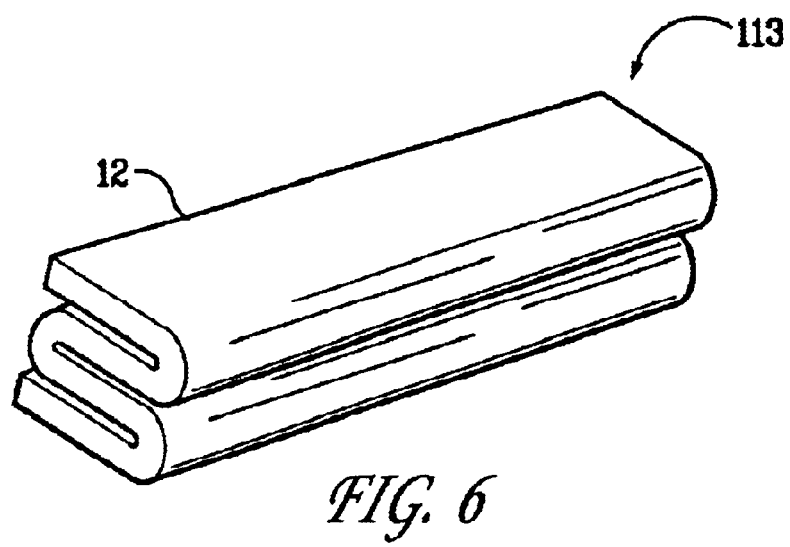
FIG. 6 is a perspective view of the resilient member of FIG. 1 in a fan folded configuration.

FIG. 6 illustrates an alternate method of folding an elongated member. In FIG. 6, the core structure 101 has been fan folded, each fold in an alternate direction, to form non-absorbent core structure 113.

Figure 7:
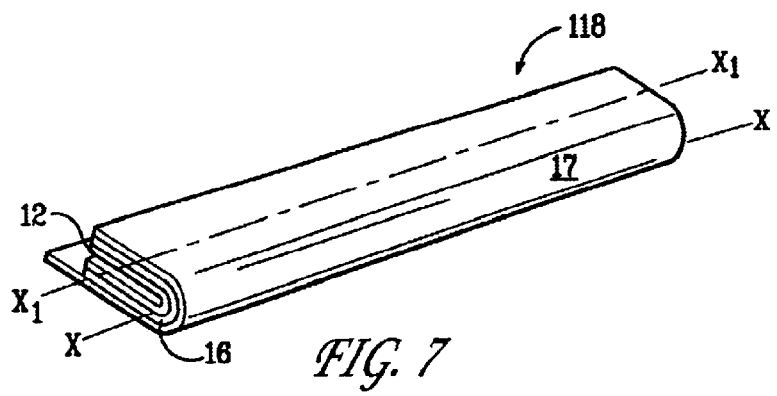
FIG. 7 is a perspective view of a structure similar to that of FIG. 3 after being folded along its longitudinal central axis.
Figure 8:
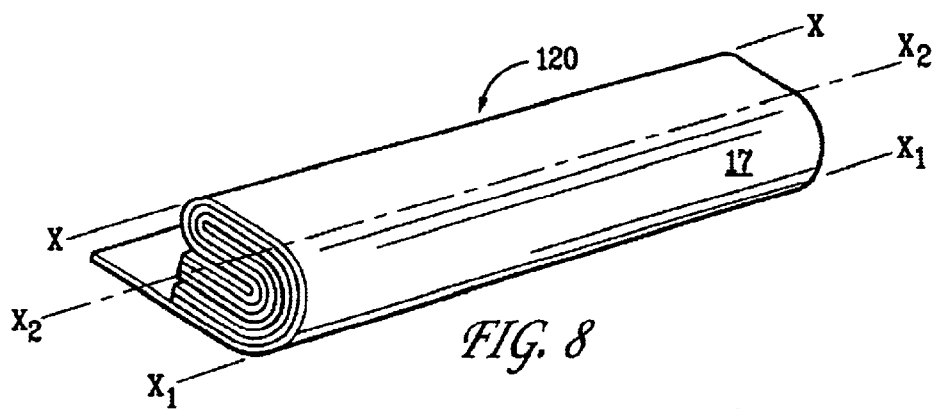
FIG. 8 is a perspective view of the structure of FIG. 7 after being folded a second time along its longitudinal central axis.
Figure 9:
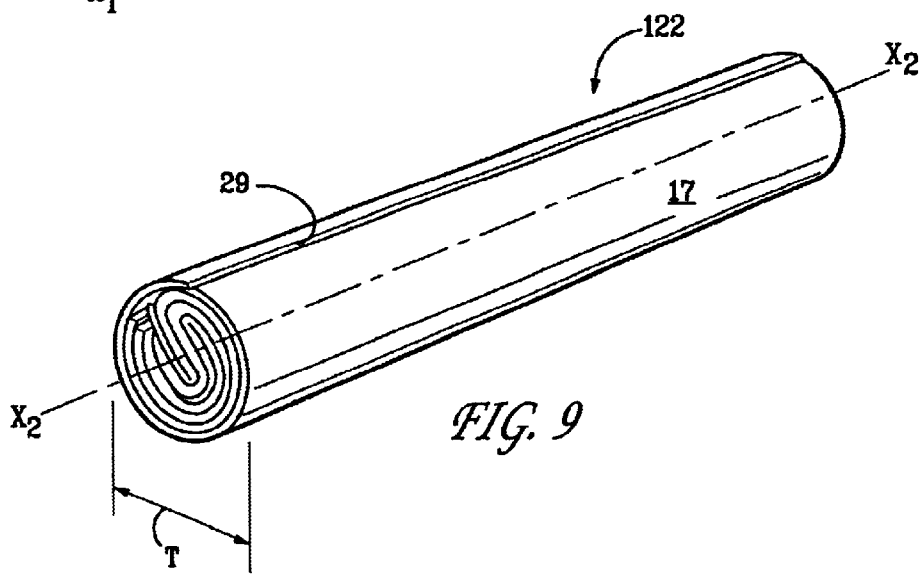
FIG. 9 is a perspective view of the twice folded elongated member showing the cover overlapping itself.

An example of a rolled elongated member is shown in FIGS. 7–9. A combination of a resilient member 12, a single non-absorbent 16 and a cover 17 (an alternate embodiment of FIG. 3 without non-absorbent 15), are folded along the central longitudinal axis X-X to obtain a folded member 118 having a central longitudinal axis $X_1$-$X_1$. The folded member 118, see FIG. 7, is then folded a second time along its central longitudinal axis $X_1$-$X_1$ to obtain an elongated member 120, having a central longitudinal axis $X_2$-$X_2$, see FIG. 8. The free end of the cover 17 can then be folded over upon itself and be bonded or attached, or left unattached if desired, to form an elongated member 122 defined by a softwind, see FIG. 9.

It should be noted that the above discussion is directed to folding the layers of material 12, 16 and 17 upon themselves to form the elongated member 122. However, the elongated member 122 could be formed by rolling, wrapping, bending and/or manipulating one or more of the layers in a known fashion to obtain an elongated member having a cylindrical, rectangular or some other shape.

Any of the elongated members 101, 102, 103, 111, 112, 113 or 122 of any of FIGS. 1–6 and 9, respectively, may be shaped to form a urinary incontinence device. A first preferred embodiment of a urinary incontinence device according to the invention has a "M-shaped" profile as is shown in FIG. 10, and a second preferred embodiment of the urinary incontinence device has a "dome-shaped" profile and is shown in FIG. 16.

Referring now to FIGS. 10 and 11, to make an "M-shaped" urinary incontinence device, an elongated member 130 matching any of the previous descriptions or equivalents is folded or bent upon itself such that the first and second ends, 24 and 26, respectively, are aligned adjacent to one another and the elongated member 22 contains at least two folds 28 and 30 therebetween, see FIG. 10. By being aligned "adjacent to one another" it is meant that the first and second ends, 24 and 26, respectively, are positioned side by side, parallel to one another or offset axially or spaced radially apart from one another, or are positioned in some type of arrangement whereby the first and second ends, 24 and 26 respectively, are close to one another. If a cover material is used in making the elongated member 130, the bonded or open edges of the cover material should be positioned to the inside when the first and second ends 24 and 26, respectively, are aligned adjacent to one another.

Preferably, the elongated member 130 will contain three folds 28, 30 and 32 which are located between the first and second ends 24 and 26, to give the elongated member a generally M-shaped profile. In the generally M-shaped profile, the elongated member 130 is folded at 28 to form a first portion 34 and is folded a second time at 30 to form a second portion 36 and a third portion 38. The first and third portions 34 and 38 respectively, preferably have approximately the same length, although their lengths can differ if desired. It is also possible to form the first, second, and third portions 34, 36, and 38 to have approximately the same length. For example, if the elongated member 130 has a length of about 6 inches (about 152 mm), each of the portions 34, 36, and 38 can have a length of approximately 2 inches (about 151 mm).

Still referring to FIG. 10, the third fold 32 provides the elongated member 22 with the generally M-shaped profile.

The third fold 32 can be positioned an equal or an unequal distance between the first and second folds, 28 and 30, respectively. When the third fold 32 is positioned an equal distance between the first and second folds, 28 and 30, respectively, the third fold 32 will be axially aligned along a central longitudinal axis Z-Z. The central longitudinal axis Z-Z, see FIG. 10, vertically divides the generally M-shaped profile of the elongated member 130 into left and right mirror images. It is also possible to form the third fold 32 closer to either the first or second folds, 28 and 30, respectively, if desired.

Referring to FIG. 11, the elongated member 130 is then compressed into a pledget 40 having an insertion end 51 and a trailing end 52. The pledget 40 can have any desired shape but preferably, it will have a generally cylindrical shape with a circular cross-sectional configuration. An alternative profile would be a rectangular cross-sectional configuration. The pledget 40 has a withdrawal member 56 as more fully described below.

The pledget 40 is an elongated member having a length $L_3$, a width $W_3$ and a depth $D_3$ which extends into the sheet. When the pledget 40 is round in cross-section, its diameter will be equal to the width dimension $W_3$ and depth $D_3$ dimension. The length $L_3$ of the pledget 40 can range from about 0.4 inches (about 10 mm) to about 4.7 inches (about 120 mm), preferably from between about 1.5 inches (about 38 mm) to about 2.5 inches (about 64 mm), and most preferably, the length $L_3$ is about 2 inches (about 51 mm). The width $W_3$ and depth $D_3$ can range from between about 0.2 inches (about 5 mm) to about 2.5 inches (about 64 mm), preferably from between about 0.5 inches (about 12.7 mm) to about 2.3 inches (about 60 mm). Most preferably, the width $W_3$ and depth $D_3$ of the pledget 40 is less than about 1.6 inches (about 40 mm).

The pledget 40 also has a dimension $R_3$ which is a diagonal line drawn between the apex of fold 28 and the bottom surface of the fold 32. This dimension $R_3$ is also equal in distance to a diagonal line drawn between the apex of fold 30 and the bottom surface of the fold 32. The dimension $R_3$ can range from between about 0.2 inches (about 5 mm) to about 1.2 inches (about 30 mm). Preferably, the dimension $R_3$ will be about 1 inch (about 25.4 mm) in length). Another way of stating the length of the dimension $R_4$ is to say that it should have a length which is equal to at least about 25 percent of the length $L_3$ of the pledget 40. This length will be sufficient to insure that the pledget 40 can laterally expand outward and provide pressure against the interior walls of the vagina.

Still referring to FIG. 11, the insertion end 51 of the pledget 40 is designed to be the first part of the pledget 40 which enters the woman's vaginal cavity. It should be noted that, while in use, the pledget 40 will be entirely positioned within the woman's vagina. The insertion end 51 will normally contain a greater amount of non-absorbent material than the trailing end 52. Even though a greater amount of material maybe present at the insertion end 51, the outside diameter of the insertion end 51 should be equal to the outside diameter of the trailing end 52. The amount of non-absorbent material in the insertion end 51 will have to be densified to a greater extent than the non-absorbent material making up the trailing end 52. By having a greater amount of material present at the insertion end 51, the urinary incontinence device 10 is better able to expand and support the musculature and the body tissue located adjacent to the urethra and facilitate urethral compression. This will eliminate the involuntary escape of urine through the urethra.

FIGS. 12–16 illustrate the construction of a dome-shaped urinary incontinence device 50. Referring to FIG. 12, the elongated member 130 is folded or bent upon itself such that the first and second ends, 24 and 26 respectively, are aligned adjacent to one another and the elongated member 130 contains a fold point 28. By being aligned "adjacent to one another" it is meant that the first and second ends, 24 and 26 respectively, are positioned side by side, parallel to one another, or offset axially or spaced radially apart from one another, or are positioned in some other type of arrangement whereby the first and second ends, 24 and 26 respectively, are close to one another.

The elongated member 130 will contain a first portion 60 located adjacent to the first end 24, a second portion 62 located adjacent to the second end 26 and a third portion 64 located between the first and second portions, 60 and 62 respectively. The first and second portions, 60 and 62 respectively, can have approximately the same length or differ in length, if desired. A length of from between about 1 inch (about 25 mm) to about 3 inches (about 76 mm) is adequate for each of the first and second portions, 60 and 62 respectively. A length of from between about 1.5 inches (about 33 mm) to about 2.5 inches (about 63 mm) is preferred for the first and second portions, 60 and 62 respectively. The third portion 64 can have a length less than, equal to or greater than the length of either the first or second portions, 60 and 62 respectively. Preferably, the third portion 64 will have a length which is slightly longer than either the first or second portions, 60 and 62 respectively. A typical elongated member 130 from which the urinary incontinence device 50 is to be formed will have a length of from between about 5 inches (about 127 mm) to about 8 inches (about 203 mm), with a length of from between about 5 inches (about 127 mm) to about 6 inches (about 152 mm) being preferred. When the elongated member 130 has a length of about 5 inches (about 127 mm), the first and second portions, 60 and 62 respectively, can have a length of about 1.5 inches (about 38 mm) and the third portion 64 can have a length of about 2 inches (about 51 mm).

Referring to FIGS. 12, 13 and 14, when the elongated member 130 is folded at point 65 and the first and second ends, 24 and 26 respectively, are aligned adjacent to one another, a closed loop 66 is formed. This closed loop 66 is made smaller or minimized to form a smaller closed loop 68 as the entire first and second portions, 60 and 62 respectively, are brought into contact with one another, see FIG. 13. The third portion 64 is then transformed into an arcuate shape by pressing or squeezing the third portion 64 down against itself to form a semi-dome or mushroom-like profile, see FIG. 14. This arcuate shape has opposite edges 72 and 74 which extend horizontally outward beyond the combined width of the first and second portions, 60 and 62 respectively.

Referring to FIG. 15, the edges 72 and 74 of the arcuate shape are folded downward and/or inward to obtain a dome-shaped tip 76. By "dome-shaped" it is meant a hemispherical configuration resembling a dome structure. The dome shape tip 76 has a higher concentration of material and therefore is denser than the remaining first and second portions, 60 and 62 respectively.

Referring to FIG. 16, the elongated member 130 is then compressed into a pledget 70 having an insertion end 80 and a trailing end 82. The pledget 70 can have any desired shape but preferably, it will have a generally cylindrical shape with a circular cross-sectional configuration. An alternative profile would be a rectangular cross-sectional configuration. The pledget 70 is an elongated member having a length $L_4$, a width $W_4$ and a depth $D_4$ which extends into the sheet. When the pledget 70 is round in cross-section, its diameter will be equal to the width dimension $W_4$ and depth $D_4$ dimension. The length $L_4$ of the pledget 40 can range from about 0.4 inches (about 10 mm) to about 4.7 inches (about 120 mm), preferably from between about 1.5 inches (about 38 mm) to about 2.5 inches (about 64 mm), and most preferably, the length $L_4$ is about 2 inches (about 51 mm). The width $W_4$ and depth $D_4$ can range from between about 0.2 inches (about 5 mm) to about 2.5 inches (about 64 mm), preferably from between about 0.5 inches (about 12.7 mm) to about 2.3 inches (about 60 mm). Most preferably, the width $W_4$ and depth $D_4$ of the pledget 40 is less than about 1.6 inches (about 40 mm).

Still referring to FIG. 16, the insertion end 80 of the pledget 70 is designed to be the first part of the pledget 70 which enters the woman's vaginal cavity. It should be noted that, while in use, the pledget 70 will be entirely positioned within the woman's vagina. Since the insertion end 80 contains the dome-shaped tip 76, the insertion end 80 will normally contain a greater amount of non-absorbent material than the trailing end 82. Even though a greater amount of material maybe present at the insertion end 80, the outside diameter of the insertion end 80 should be equal to the outside diameter of the trailing end 82. The amount of non-absorbent material in the insertion end 80 will have to be densified to a greater extent than the non-absorbent material making up the trailing end 82. By having a greater amount of material present at the insertion end 80, the urinary incontinence device 50 is better able to expand and support the musculature and the body tissue located adjacent to the urethra and facilitate urethral compression. This will eliminate the involuntary escape of urine through the urethra.

When the pledget 70 is formed, the resilient member 12, the non-absorbents, and/or the cover 17, if present, are all compressed. The pledget 40 can be compressed radially and lengthwise or it can be compressed only in the radial direction.

Referring now to FIGS. 11 and 16, the compressed pledgets 40 and 70 of either of the embodiments are pierced at their trailing ends 52 and 82, respectively, to form an aperture or opening 54 which extends partially or completely through the first and second portions, 60 and 62 respectively. The aperture 54 can be formed perpendicular to the central longitudinal axis Z-Z or at an angle thereto. Preferably, the aperture 54 is spaced a short distance from the first and second ends, 24 and 26 respectively. The aperture 54 can be located a distance of from between about 0.1 inches (about 2.5 mm) to about 0.5 inches (about 12.7 mm) from the first and second ends, 24 and 26 respectively. Most preferably, the aperture 54 is located about 0.25 inches (about 6.4 mm) from each of the first and second ends, 24 and 26 respectively. The aperture 54 is designed to allow a withdrawal member 56 to be looped therethrough and be secured to its respective pledget. The withdrawal member 56 will assist in removing the expandable urinary incontinence device 10 or 50 from a woman's vagina. The aperture 54 can be formed with a needle, an awl or some other type of piercing device known to those skilled in the art. The withdrawal member 56 is threaded through the aperture 54 and looped upon itself so as to cinch it secure to the elongated member 130. The free ends of the withdrawal member 56 are then tied in a knot 58 to assure that the withdrawal member 56 will not separate from the pledget 40. The knot 58 also serves to prevent fraying of the withdrawal member 56 and to provide a place or point where a woman can grasp the withdrawal member 56 when she is ready to remove the expandable urinary incontinence device 10 from her vagina.

It should be noted that the withdrawal member 56 holds the first and second ends, 24 and 26 respectively, in direct contact with one another and will limit the amount they can expand while positioned within the woman's vagina. It should also be noted that the withdrawal member 56 can be secured to and/or attached to various areas of its respective pledget and can pass through one or more of the resilient member 12, the non-absorbent layers, the cover 17, if present, or through all three members, if desired. The aperture 54 can alternatively be formed in the elongated member 130 before it is compressed and the withdrawal member 56 can be attached either before the elongated member 130 is compressed or after the elongated member 130 is compressed into the pledget 40.

The withdrawal member 56 can be constructed from various types of strings, threads or ribbons. A thread or ribbon made from 100 percent cotton fibers works well. The withdrawal member 56 should have a length which extends beyond the end of the expandable dome-shaped urinary incontinence device 10 of from between about 2 inches (about 51 mm) to about 8 inches (about 203 mm), preferably, from between about 4 inches (about 102 mm) to about 6 inches (about 152 mm), and most preferably, about 5 inches (about 127 mm). The withdrawal member 56 can be dyed and/or treated with an anti-wicking agent, such as wax, before being secured to its respective pledget. The anti-wicking agent will reduce and hopefully prevent body fluids from wicking along the withdrawal member 56 and contacting the inner surface of a woman's undergarment. A dry, clean withdrawal member 56 is preferred by the user, especially when she goes to remove the expandable urinary incontinence device from her vagina.

Figures 17, 18:
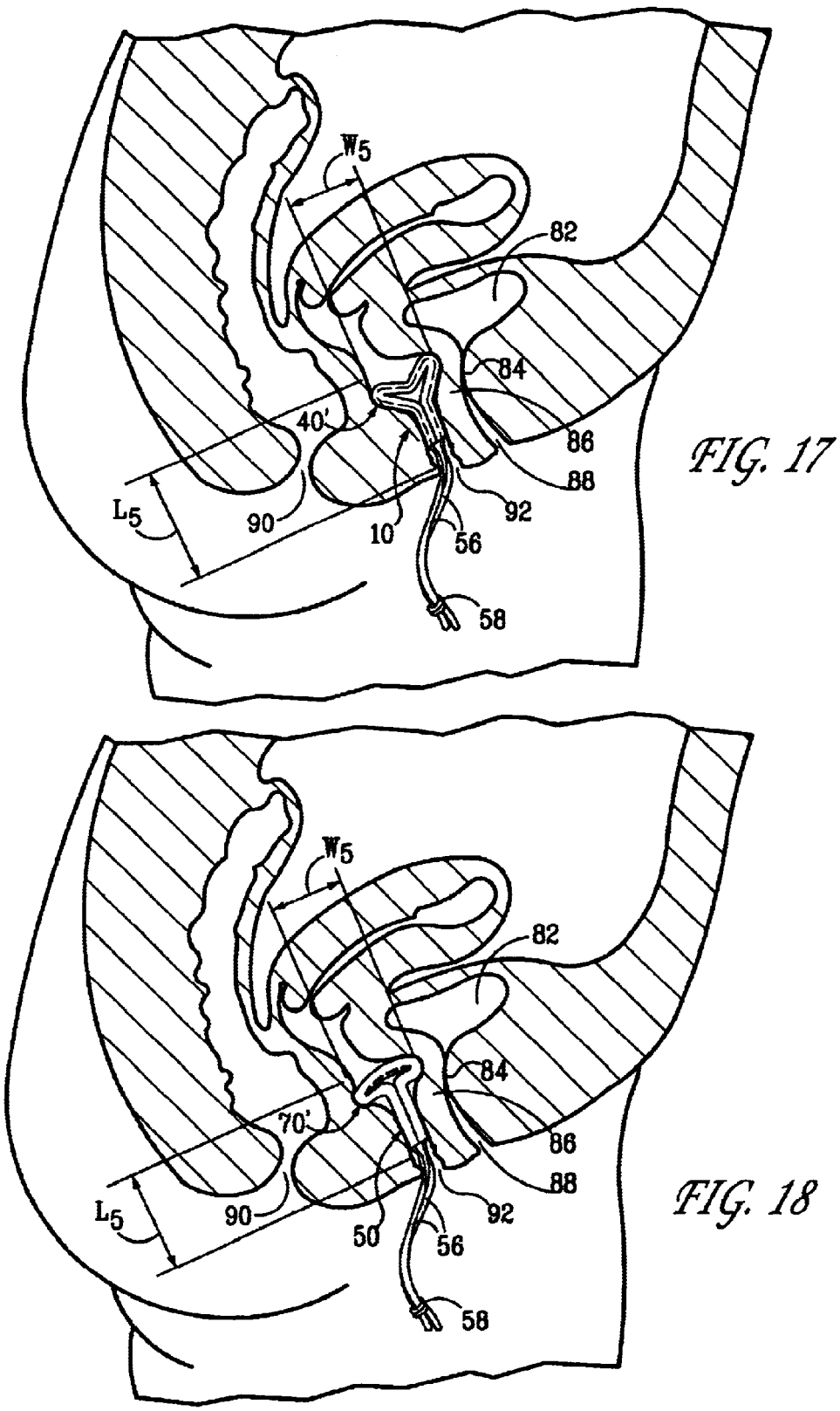
FIG. 17 is a mid-sagittal section of a human torso showing the expandable M-shaped urinary incontinence device positioned in the vagina and expanded to provide support for the musculature and tissue near the urethro-vaginal myofascial region and the urethra.
FIG. 18 is a mid-sagittal section of a human torso showing the expandable dome-shaped urinary incontinence device positioned in the vagina and expanded to provide support for the musculature and tissue near the urethro-vaginal myofascial region and the urethra.

The use of the urinary incontinence devices 10 and 50 are illustrated in FIGS. 17 and 18, respectively. In FIG. 17, the compressed pledget 40 is depicted having been inserted into a woman's vagina 92 and the pledget 40 is shown in an expanded state 40', while in FIG. 18, the compressed pledget 70 is depicted having been inserted into a woman's vagina 92 and the pledget 70 is shown in an expanded state 70'. The expanded pledgets each have a length $L_5$ and a diameter or width $W_5$. The first and second ends, 24 and 26 respectively, will stay together by the attachment of the withdrawal member 56. While within the vaginal cavity 92, the resilient member 12 will expand thereby causing the M-shape or the dome-shape to spring or expand outward and/or upward and spread across a portion of the internal vaginal space. The urinary incontinence devices 10, 50 should be positioned below the cervix. The resilient, elastic and flexible characteristics of the resilient member 12 enables the pledgets 40, 70 to recover quickly from their compressed and deformed shape. This allows the urinary incontinence devices 10 and 50 to intimately contact and conform more ideally to the space within the vaginal walls and press against the inside anterior and posterior and right and left lateral walls and convolutions of a woman's vagina 92.

A woman's urethra 88 is located adjacent to and anterior to the vagina 92. The woman's anus 90 is located on the posterior side of the vagina 92. The urethra 88 is a passageway which provides a means of removing urine from the woman's body. The urethra 88 is a conduit for removing urine which has accumulated in the woman's bladder 82 to an external orifice located at the lower end of the urethra 88. A urinary sphincter muscle 84 is situated at the upper portion of the urethra 88 adjacent to the bottom surface of the bladder 82. The sphincter muscle 84 operates to prevent the involuntary loss of urine. However, after birthing and with age the pelvic floor muscles begin to sag and the cross-sectional configuration of the sphincter muscle can change from a circular profile to a non-circular profile. Such a change increases the likelihood that a woman will experience involuntary urine loss. Between the vagina 92 and the urethra 88 is the urethro-vaginal myofascial area 86. This area 86 is made up of musculature and body tissue and the body tissue is extremely pliable. The vagina 92 contains a plurality of rugosities (not shown) which line its inside walls. The rugosities consist of wrinkles or creases in the body tissue which allows for expansion and contraction of the side walls of the vagina 92.

Comparing the compressed pledget 40, shown in FIG. 11, to the expanded pledget 40', shown in FIG. 16, as well as the compressed pledget 70, shown in FIG. 16, to the expanded pledget 70', shown in FIG. 18, one will quickly recognize that the width $W_5$ of the expanded pledgets are much greater than the widths $W_3$ and $W_4$ of their respective compressed pledgets. In addition, the shape of the expanded insertion ends are of a larger diameter or dimension than in the compressed pledgets. Furthermore, the length $L_5$ of the expanded pledget 62 will be equal to or slightly larger than the length $L_4$ of the compressed pledget 40. The thickness $D_3$ of the elongated member 130 or dimension in the z-direction should range from between about 0.5 inches (about 13 mm) to about 1.5 inches (about 38 mm). This distance will increase once the urinary incontinence devices 10 or 50 are inserted into the vagina 92 due to the expansion of the resilient member. As the pledgets 40, 70 expand by the action of the resilient member 12, to their respective expanded states 40', 70', the expanded pledget will allow for pressure transmission across body tissue and in particular, in the urethro-vaginal myofascial area 86. This action will provide a stable backdrop to allow the woman's urethra 88 to become compressed upon itself when intra-abdominal pressure increases. In other words, a part of the urethra 88 which is about 1.5 inches (about 38 mm) long and through which urine flows, will be compressed or pinched upon itself thereby preventing the urine from passing through. In addition, support will be provided to the region near the sphincter muscle 84 so that it has a higher tendency to maintain a circular cross-sectional configuration and operate properly. One or both of these actions will reduce and/or prevent involuntary urine loss due to stress urinary incontinence.

Although not shown in any of the drawings, it is contemplated that the compressed pledgets 40, 70 can be housed in a paper, cardboard or plastic applicator to facilitate insertion of the urinary incontinence device 10 or 50 into a woman's vagina 92. The applicator can be constructed of one or more hollow tubes which will retain the urinary incontinence device 10 or 50 at a set diameter and/or cross-sectional configuration until the user is ready to use the product Furthermore, insertion of the urinary incontinence device 10 or 50 from the applicator into the human body can be accomplished by using a plunger, such as a two piece applicator, or by digital insertion whereby the user can use one of her fingers. Particularly preferred applicators are disclosed in U.S. application Ser. No. 09/675,458, entitled "Incontinence Insert Applicators and A Method of Making the Same," filed Sep. 28, 2000, the entire disclosure of which is incorporated herein by reference in its entirety.

Figure 19:
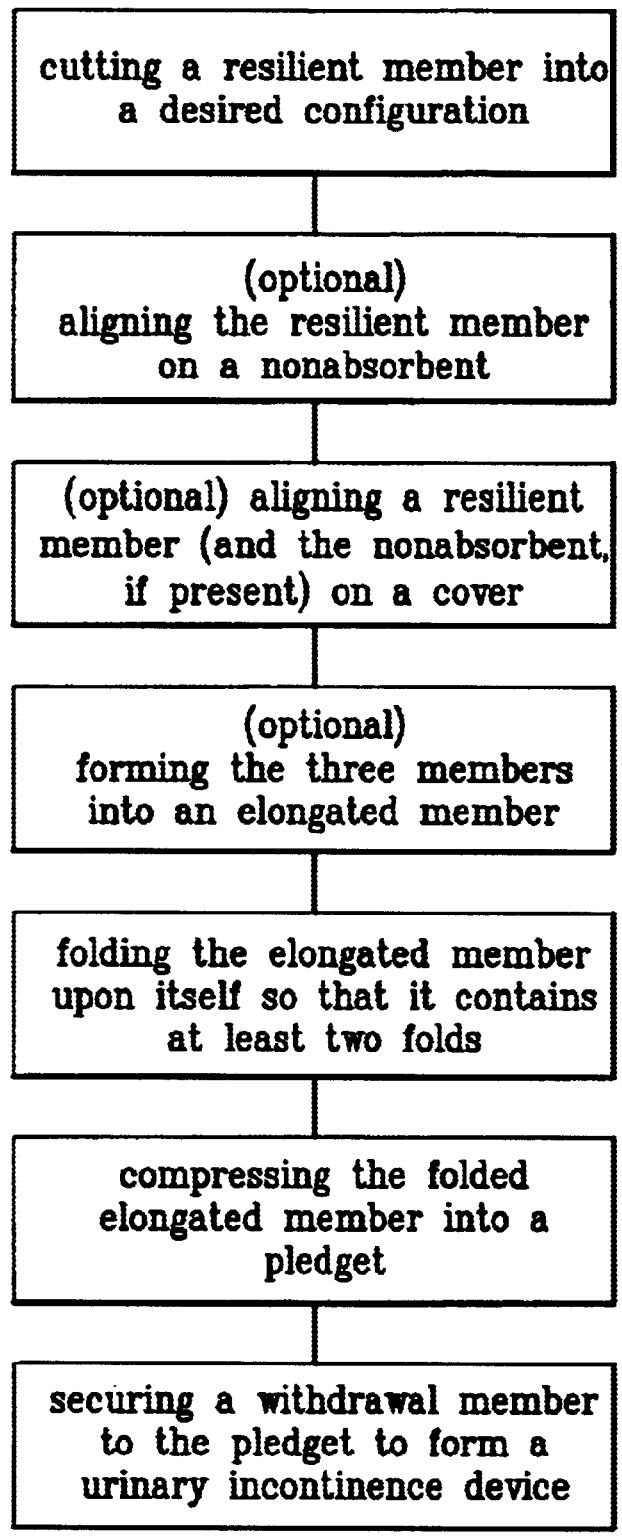
FIG. 19 is a flow diagram of a method of forming the expandable M-shaped urinary incontinence device.

The method of forming the expandable urinary incontinence device 10 or 50 will now be explained with reference to the flow diagrams shown in FIGS. 19 and 20, respectively.

The method includes the steps of forming or cutting a resilient member 12 into a desired geometrical shape. A preferred shape for the resilient member 12 is a rectangle although many other shapes will work. The resilient member 12 will have a desired length, width and thickness.

Optionally, one or more non-absorbents 13, 14 may be aligned on either surface of the resilient member 12. The non-absorbents 13, 14 may be in the form of a fibrous carrier, or in the form of a cover material. One of the non-absorbents is adjacent a first surface of the resilient member 12, and the other non-absorbent is adjacent a second surface of the resilient member 12. If the non-absorbents are fibrous carriers, another optional layer, a cover 17, may be placed adjacent one of the non-absorbents.

The multiple layers, if present, are combined into a laminate-like structure. The layers should be substantially coextensive in their length and width dimensions. The length and width dimensions of any of the structures, depicted in FIGS. 1–3, or their alternative embodiments, may be such that structures may be used an elongated member to form a urinary incontinence device. Alternately, the structures may first be folded and/or rolled into an elongated member suitable to be shaped into a urinary incontinence device.

The structure of FIG. 1 is depicted as folded in FIG. 4. The structure of FIG. 2 is depicted as folded in FIG. 5. The resulting structures 111 and 112, respectively, may be used an elongated member for shaping a urinary incontinence device, or may be further folded (not shown) before being shaped into a urinary incontinence device.

The structures may also be folded and/or rolled, as depicted in FIGS. 7–9. A non-absorbent 16, along with the cover 17 are folded around the resilient member 12. One method of folding is to fold the non-absorbent 16 and the cover 17, if present, transversely upon themselves such that a folded member 118 is formed and the resilient member 12 is now located adjacent to the longitudinal fold line $X_1$-$X_1$. The folded member 118 can then be folded a second time in a similar fashion to yield an elongated member 120 as depicted in FIG. 8. When a cover 17 is present, the cover 17 can be wrapped or folded over upon itself and be bonded or attached to another portion of the cover 17 to form an elongated member 122, see FIG. 9.

It should be noted that the different materials forming the resilient member 12, the non-absorbent 16 and the cover 17 can be folded one or more times to obtain a predetermined diameter or cross-sectional configuration. Furthermore, the materials can be rolled, wrapped, bent or otherwise manipulated to arrange them into an elongated member.

Any of the elongated members above may be used to form a urinary incontinence device. Two preferred shapes for the urinary incontinence device are the "M-shaped" profile and the "dome-shaped" profile.

To construct a urinary incontinence device having a "M-shaped" profile, an elongated member is folded or bent along its length to arrive at a generally triangular profile when viewed perpendicular to the folds. Preferably, the elongated member is folded such that it contains three folds and acquires a generally M-shaped profile. An example of the generally M-shaped profile is depicted in FIG. 10. The location of the folds 28, 30, and 32 can vary but one preferred embodiment is depicted in FIG. 11.

After the elongated member has been folded into a generally triangular or M-shaped profile, it is compressed radially into a pledget 40, as depicted in FIG. 11. The elongated member can be compressed only in the radial direction or it can be compressed both axially and radially. Since the pledget 40 contains more material at the insertion end 50 than at the trailing end 52, the insertion end 50 will be denser since the pledget 40 has the same diameter or cross-sectional area throughout its entire length. This added material at the insertion end 50 will assure that as the pledget 40 opens and expands, once it is inserted into a women's vagina, that it will provide a stable backdrop for the urethra and be able to provide the required pressure against the neighboring body tissue located in the urethro-vaginal mysofascial area so as to restrict the involuntary flow of urine through the urethra.

Figure 20:
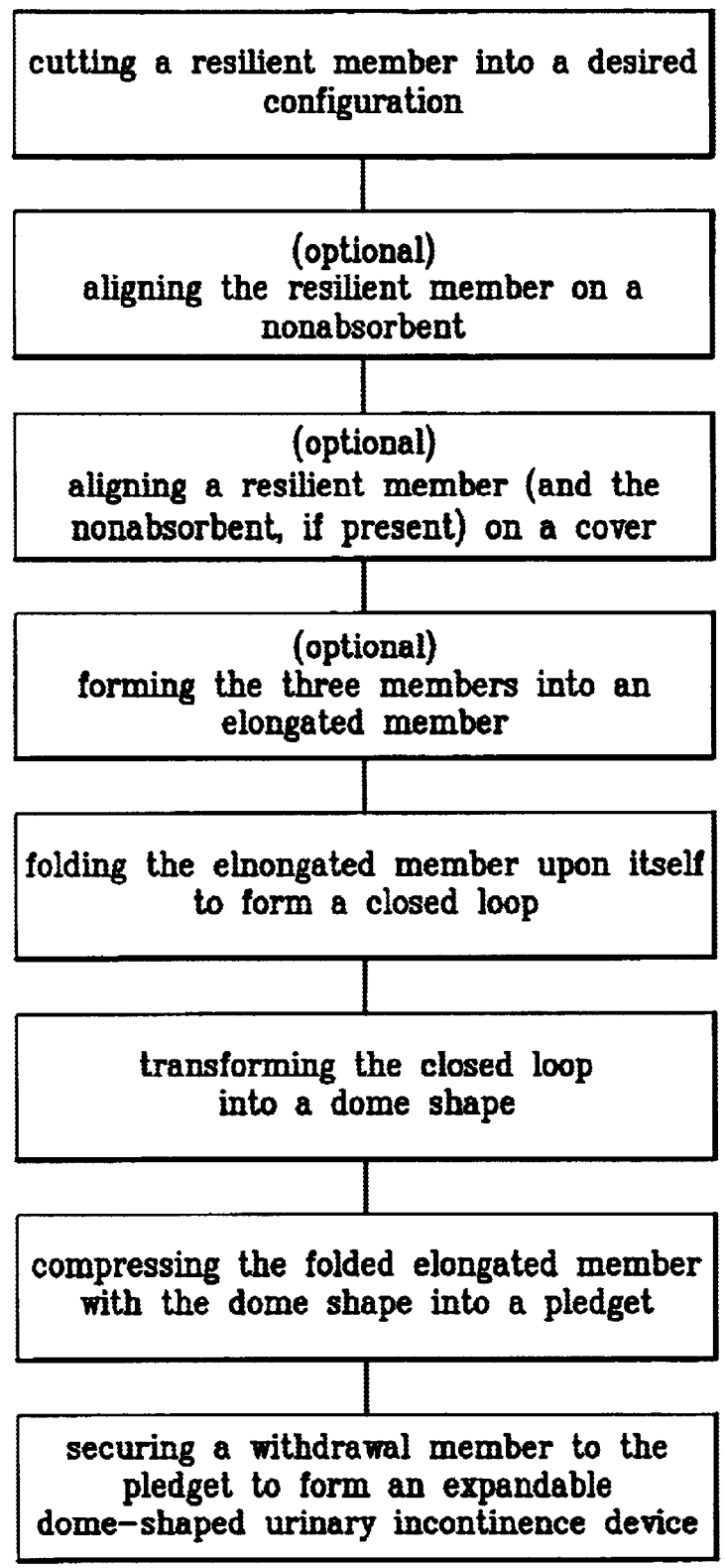
FIG. 20 is a flow diagram of a method of forming an expandable dome-shaped urinary incontinence device.

Alternately, as shown in FIG. 20, once an elongated member 130 is formed, it is folded or bent at a fold point 65 so that the first and second ends, 24 and 26 respectively, can be aligned adjacent to one another. Preferably, the elongated member 130 is folded in half and a closed loop 66 is formed as the first and second portions, 60 and 62 are aligned parallel to one another, see FIG. 12. The first and second portions, 60 and 62 respectively, are then brought together along their entire length and the closed loop 66 is reduced in size to a smaller loop 38, see FIG. 13. At this point, the third portion 64 is pressed or squeezed downward upon itself in the direction of the first and second portions, 60 and 62 respectively. This action creates a semi-dome or mushroom-like profile, see FIG. 14, wherein the edges 72 and 74 of the third portion 64 extend outward beyond the thickness of the first and second portions, 60 and 62 respectively. The transformation of the third portion 64 into the semi-dome or mushroom-like profile is continued by folding or bending the opposite edges 72 and 74 downward and/or inward against the outer surfaces of the first and second portions, 60 and 62 respectively, to form a dome-shaped tip 76, see FIG. 15. This dome-shaped tip 76 contains more non-absorbent material than is present in a similar area of the first and second portions, 60 and 62 respectively, and therefore is denser.

After the dome-shaped tip 76 has been formed, the elongated member 130 is compressed radially into a pledget 70, see FIG. 16. The elongated member 130 can be compressed only in the radial direction or it can be compressed both axially and radially. Since the pledget 78 contains more material at the insertion end 80 than at the trailing end 82, the insertion end 80 will be denser since the pledget 70 has the same diameter or cross-sectional area throughout its entire length. This added material at the insertion end 80 will assure that as the pledget 70 opens and expands, once it is inserted into a woman's vagina, that it will provide a stable backdrop for the urethra and be able to provide the required pressure against the neighboring body tissues located in the urethro-vaginal myofascial area 86 so as to restrict the involuntary flow of urine through the urethra.

The compressed pledgets can then have a hole or aperture 54 formed through its trailing ends 52, 82, respectively, for receiving a withdrawal member 56. The aperture 54 can be formed with a needle, an awl or some other mechanical, electrical, chemical, hydraulic or pneumatic means. The aperture 54 should be aligned parallel to the first and second ends, 24 and 26 respectively, of the elongated member 130 and be sufficiently spaced apart from the ends 24 and 26 to insure that as one pulls on the withdrawal member 56 that it will not tear through the material and be separated from the pledgets. The withdrawal member 56 can be inserted through the aperture 54 and be looped upon itself to cinch it tight against the pledgets. The pair of free ends of the withdrawal member 56 can then be tied in a knot 58 for added assurance that the withdrawal member 56 will not separate from the pledgets.

While the invention has been described in conjunction with several specific embodiments, it is to be understood that many alternatives, modifications and variations will be apparent to those skilled in the art in light of the aforegoing description. Accordingly, this invention is intended to embrace all such alternatives, modifications and variations which fall within the spirit and scope of the appended claims.

What is claimed is:

1. A nonabsorbent urinary incontinence device comprising:

a resilient member; and a non-absorbent;

said non-absorbent and said resilient member being formed into a layered elongated member having a non-absorbent layer and a resilient member layer, wherein a first surface of said resilient member is adjacent and substantially coextensive with a surface of said non-absorbent; said layered elongated member having a first end, a second end, a first portion located adjacent to said first end, a second portion located adjacent to said second end, and a third portion located between said first and second portion, said elongated member being folded upon itself such that said first and second ends are aligned substantially adjacent to one another, wherein said elongated member is adapted to support musculature and body tissue in an urethro-vaginal myofacial area.

2. The urinary incontinence device of claim 1, wherein said third portion is formed into a closed loop, said first and second portions being brought together to minimize said closed loop, said third portion being transformed into a dome shape.

3. The urinary incontinence device of claim 1, wherein said elongated member contains at least two folds between said first end and said second end to form a generally M-shaped profile.

4. The urinary incontinence device of claim 1, further comprising a second non-absorbent layer, said second non-absorbent layer adjacent a second surface of said resilient member opposite said first surface.

5. The urinary incontinence device of claim 1, wherein said layered elongated member is folded along a longitudinal axis before being folded upon itself.

6. The urinary incontinence device of claim 5, where said layered elongated member is fan folded.

7. The urinary incontinence device of claim 1, wherein said layered elongated member is formed into a soft wind before folding said layered elongated member upon itself to form a closed loop.

8. The urinary incontinence device of claim 1, wherein said layered elongated member is compressed into an elongated pledget.

9. The urinary incontinence device of claim 8, wherein said resilient member is capable of expanding such that the pledget provides a supportive backdrop for a woman's urethra when inserted into a vagina.

10. The urinary incontinence device of claim 1, wherein said non-absorbent comprises a fibrous carrier.

11. The urinary incontinence device of claim 1, wherein said non-absorbent comprises a cover fabric.

12. A nonabsorbent urinary incontinence device comprising:

a non-absorbent resilient member formed into an elongated member, said elongated member having a first end, a second end, a first portion located adjacent to said first end, a second portion located adjacent to said second end, a third portion located between said first and second portions, and a closed loop, said elongated member being folded upon itself such that said first and second ends are aligned substantially adjacent to one another and are brought together to minimize said closed loop, said third portion being transformed into a dome shape and wherein said elongated member is adapted to support musculature and body tissue in an urethro-vaginal myofacial area.

13. The urinary incontinence device of claim 12, wherein said third portion is formed into a closed loop, said first and second portions being brought together to minimize said closed loop, said third portion being transformed into a dome shape.

14. The urinary incontinence device of claim 12, wherein said elongated member contains at least two folds between said first end and said second end to form a generally M-shaped profile.

15. The urinary incontinence device of claim 12, wherein said elongated member is compressed into an elongated pledget.

16. The urinary incontinence device of claim 15, wherein said resilient member is capable of expanding such that the pledget provides a supportive backdrop for a woman's urethra when inserted into a vagina.

17. A method of making a nonabsorbent urinary incontinence device, the method comprising:

a. cutting a resilient member into a desired configuration;

b. aligning a first surface of the resilient member upon a first surface of a non-absorbent such that said resilient member and said non-absorbent are substantially coextensive to form an elongated member having first and second ends;

c. folding said elongated member upon itself such that said first and second ends are aligned adjacent to one another; and d. compressing said elongated member into an elongated pledget having an insertion end and a trailing end with said resilient member located at least in said insertion end, whereby said resilient member is capable of expanding at least a portion of said pledget such that the pledget is adapted to support musculature and body tissue in an urethro-vaginal myofacial area.

18. The method of claim 17, further comprising attaching a withdrawal member to said trailing end of said pledget.

19. The method of claim 17, wherein a portion between said first and second ends is formed into a dome-shaped closed loop.

20. The method of claim 17, wherein said elongated member contains at least two folds between said first end and said second end to form a generally M-shaped profile.

* * * * *